United States Patent [19]

Chittenden

[11] 4,363,321
[45] Dec. 14, 1982

[54] I.V. ADMINISTRATION FLOW RATE GAUGE

[75] Inventor: Richard M. Chittenden, Grayslake, Ill.

[73] Assignee: Abbott Laboratories, North Chicago, Ill.

[21] Appl. No.: 332,070

[22] Filed: Dec. 18, 1981

Related U.S. Application Data

[63] Continuation of Ser. No. 157,919, Jun. 9, 1980, Pat. No. 4,312,342.

[51] Int. Cl.³ .............................................. A61M 5/00
[52] U.S. Cl. ................................................ 128/214 R
[58] Field of Search .......... 128/214 R, 214 C, 214 D, 128/214 E, 213, 227; 137/391, 430, 433; 73/194 R, 195, 196, 861.63

[56] References Cited

U.S. PATENT DOCUMENTS

| | | | |
|---|---|---|---|
| 2,337,921 | 12/1943 | Petroe | 73/861.63 |
| 2,439,723 | 4/1948 | Engdahl | 73/196 |
| 3,326,041 | 6/1967 | Reed | 73/213 |
| 3,898,637 | 8/1975 | Wolstenholme | 128/214 E X |
| 3,982,534 | 9/1976 | Buckman | 128/214 C |
| 4,079,737 | 3/1978 | Miller | 128/214 R |
| 4,186,740 | 2/1980 | Guerra | 128/214 R |
| 4,269,222 | 5/1981 | Palti | 128/214 C X |

OTHER PUBLICATIONS

Brochure: Travenol Infusion Controller, Published Mar. 1979.
Brochure: The IVAC 230 Controller, IVAC Corp. Jun. 1979.

Primary Examiner—John D. Yasko
Attorney, Agent, or Firm—Robert S. Beiser; Robert L. Niblack

[57] ABSTRACT

An apparatus for measuring the flow of medical liquids within an intravenous solution administration set comprises a primary tube, a secondary tube and a tertiary tube. A constricter mechanism is positioned in the primary tube proximate the opening to the tertiary tube in order to restrict the flow of liquid therethrough. As a result a pressure differential is created between the secondary tube and the tertiary tube when liquid flows through the primary tube. At least a portion of the secondary or tertiary tubes are transparent in order to determine the relative position of liquid in the tube. A series of markings on the tubes represent designated rates of flow. Consequently, the relative position of the liquid is used to display the rate of flow within the system.

7 Claims, 4 Drawing Figures

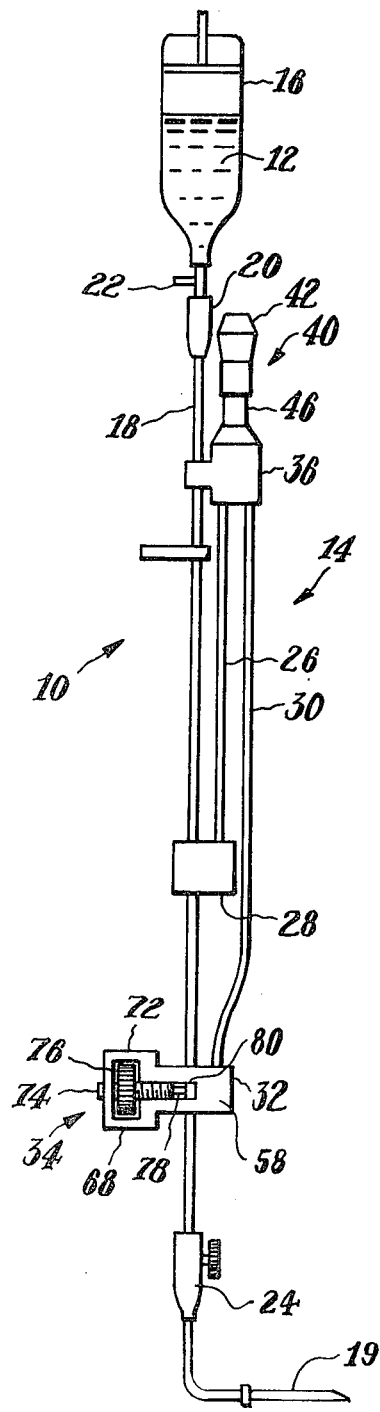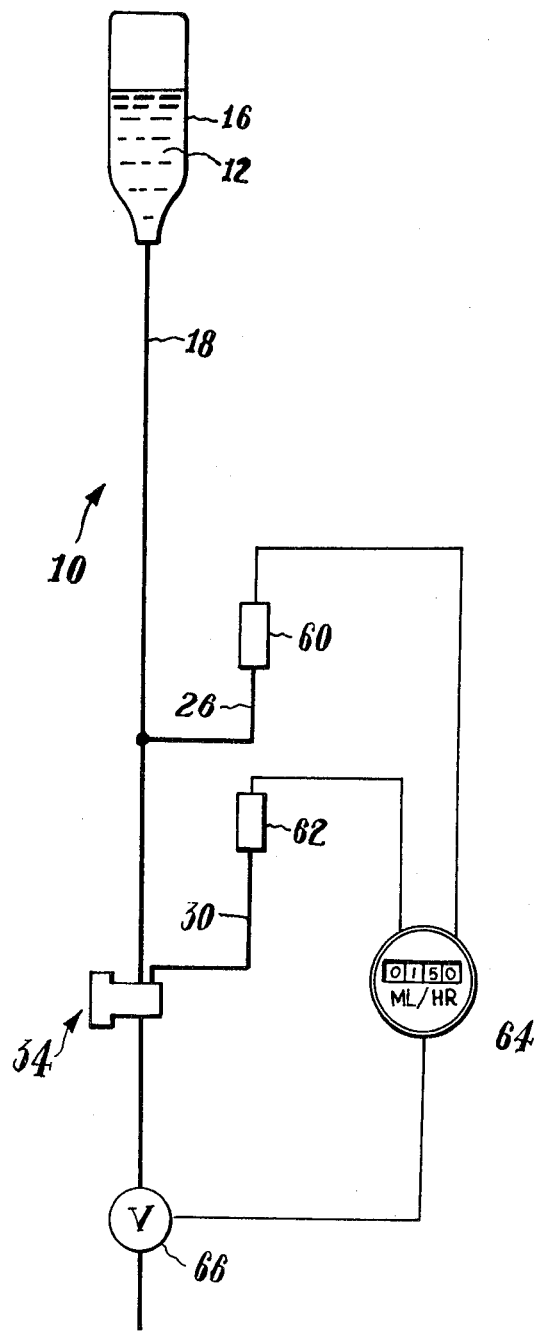
FIG. 1
FIG. 3

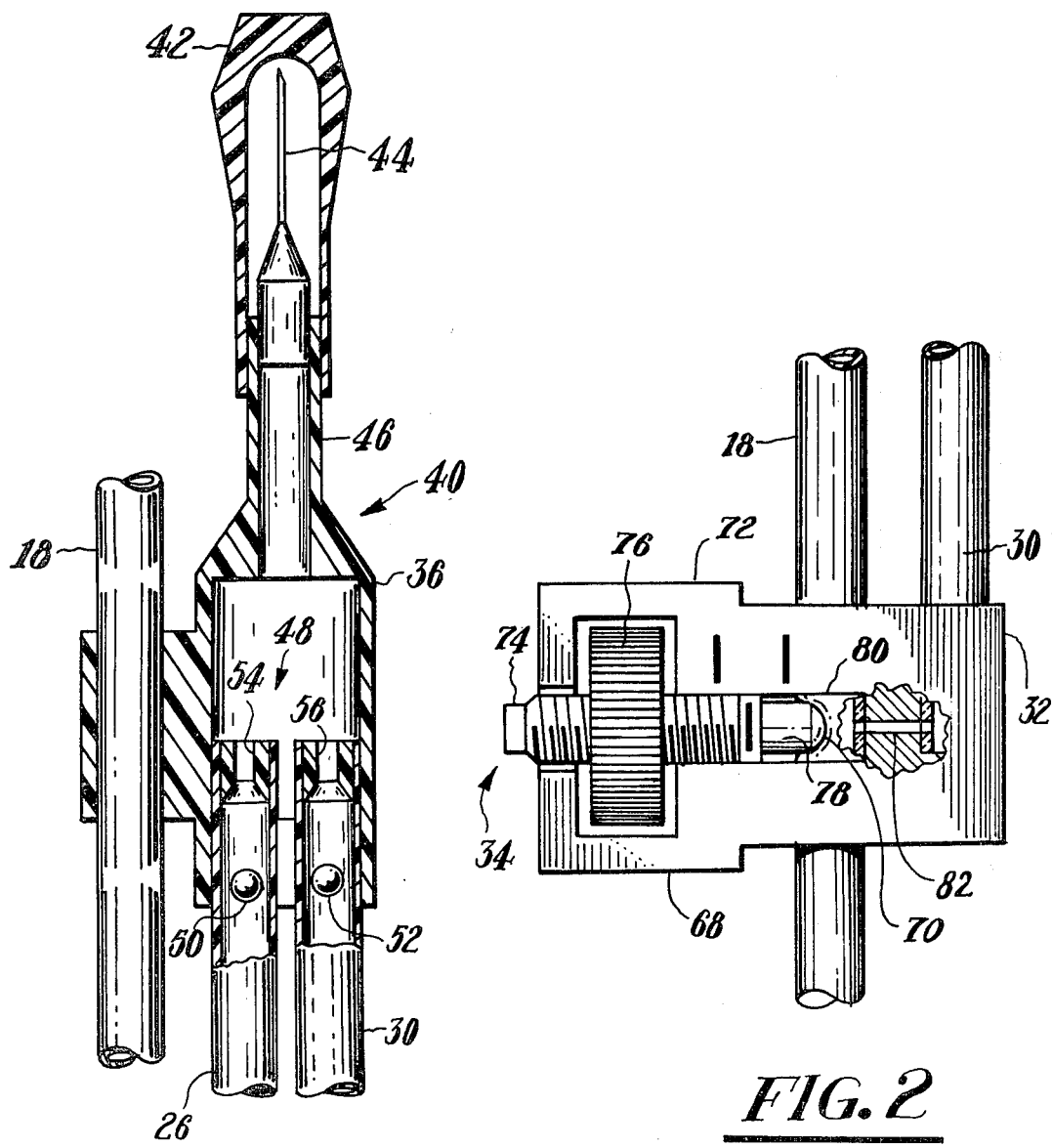

I.V. ADMINISTRATION FLOW RATE GAUGE

This is a continuation, of application Ser. No. 157,919, filed June 9, 1980 now U.S. Pat. No. 4,312,342.

BACKGROUND OF THE INVENTION

The present invention relates generally to flow rate gauges and in particular to a flow rate gauge adapted for use with an intravenous administration set.

One of the major advances in medical science in recent years has been the wide use of intravenous solutions for administering nutrients and medicaments to hospitalized patients. A continuing problem in this area, however, has been administering said solutions at a controlled rate in order to prevent undesired side effects. Several devices are presently available for administering intravenous solution at a controlled rate. The most common of these are roller clamp mechanisms affixed about a length of flexible tubing which extends from a solution container to an intravenous needle. A continuing difficulty has remained however, in measuring the rate of flow of liquid from the container.

Commonly known means of measuring flow may be seen in the following U.S. patents and publications:

- U.S. Pat. No. 2,439,723—R. B. Engdahl—FLOW METER—Issued Apr. 13, 1948;
- U.S. Pat. No. 3,326,041—R. D. Reed—APPARATUS FOR DEVELOPING DIFFERENTIAL PRESSURES IN A CONDUIT LINE—Issued June 20, 1967;
- U.S. Pat. No. 3,898,637—Eugene B. Wolstenholme—DETECTION MEANS FOR GAS ENTERING HUMAN BLOOD SYSTEMS FROM EXTRACORPORIAL TUBING—Issued Aug. 5, 1975;
- U.S. Pat. No. 4,079,737—John J. Miller—CONTROL VALVE FOR INFUSION SYSTEM—Issued Mar. 21, 1978;
- Brochure: Travenol Infusion Controller—Parenteral Products Division, Travenol Laboratories, Inc., Published March, 1979;
- The IVAC 230 Controller, IVAC Corporation, 11353 Sarentino Valley Road, San Diego, Calif.—June, 1979.

Despite the advances these patents and articles represent, a continuing problem exists in producing a low cost intravenous solution flow rate gauge which can easily and accurately measure the rate of liquid flow within an I.V. system.

Accordingly, it is an advantage of the invention to provide a low cost flow rate gauge for measuring liquid flow. It is an additional advantage of the invention to provide such a gauge which may be utilized with intravenous solutions. It is a further advantage of the invention to provide such a gauge which prevents the passage of air, bacteria or contaminants into an intravenous administration set.

SUMMARY OF THE INVENTION

The present invention is an improved device for measuring liquid flow within a gravitational flow system. The device comprises a primary tube, a secondary tube and a tertiary tube. The primary tube is connected at its distal end with a source of liquid, such as a container of intravenous solution, and extends downwardly therefrom. The secondary tube is connected at its proximal end with the proximal end of the primary tube, and extends vertically from that point in parallel with the primary tube. A tertiary tube connected at its proximal end with the primary tube at the proximal end of the primary tube is also disposed vertically and parallel to the primary tube. A constricting mechanism is used to create a venturi effect in the primary tube proximate the opening to the tertiary tube. As a result of this constriction, when liquid flows through the primary tube, a pressure differential is created between the secondary tube and the tertiary tube. A connection between the distal end of the secondary and tertiary tube allows the passage of air, and thereby allows relative movement of liquid within the two tubes. A series of markings or visual indicia are systematically displayed on the secondary and/or the tertiary tubes in order to determine the relative position of said liquids within the tubes to a known standard. As a result the rate of flow of the liquid within the primary tube may be determined.

The previously mentioned constricting mechanism may comprise any of several types of adjustable clamps such as a screw clamp, which is used for varying the size of the orifice within the primary tube. Adjustment of the sensitivity of the flow rate gauge is thereby allowed. The screw clamp adjustably compresses the primary tube and thereby constricts the flow of liquid therethrough. As a result the relative pressure in the tertiary tube may be varied.

An additional feature of the invention is a venting mechanism for dispensing air from the secondary and tertiary tubes, so that both tubes can be filled to their midpoint. In a preferred embodiment the venting mechanism comprises a flexible penetrable bulb extending from the connection between the secondary and tertiary tubes. A cannula or hollow needle is fixedly attached within the bulb and is arranged for selective penetration of the bulb so as to release air from within the secondary and tertiary tubes as required. Alternatively, the venting mechanism may comprise a port extending from the connection between the secondary and tertiary tubes having a plurality of venting apertures thereon. A cap is moveably attached to the port. When the cap is displaced, the venting apertures are exposed to the atmosphere. Air within the secondary and tertiary tubes may thereby be vented as desired. In this embodiment, the cap may be threadedly attached to the port or may be spring-biased in a closed position. The tubes may be vented by pulling the cap upwardly against the spring bias, thereby exposing the vents.

In a preferred embodiment, the gauge is constructed of a plurality of flexible transparent plastic tubes which facilitate viewing of the liquid within the device. In one embodiment, a valve mechanism within the tubes which facilitates viewing of the liquid within the secondary tube prevents the flow of liquid from the secondary tube into the tertiary tube and hence the passage of air from the tertiary tube back into the primary tube. This valve may comprise a hydrophobic membrane or a ball-check valve. Similarly, the tertiary tube may include a valve for preventing passage of air from the tertiary tube into the primary tube such as a hydrophilic membrane.

An additional feature of the invention is the use of a pair of pressure transducers attached to the secondary and tertiary tubes, which are connected to a gauge for measuring the relative pressure within each tube. This pressure can be converted to a flow rate, which is then indicated on an alpha-numeric display. Additionally, the pressure gauge may provide an electrical signal to an electrically actuated valve for controlling the rate of flow of liquid through the primary tube.

BRIEF DESCRIPTION OF THE DRAWINGS

FIG. 1 of the drawings is a front view of a gravitational flow system for medical liquids, including an apparatus for measuring the rate of flow of liquid within the system.

FIG. 1A of the drawings is a vertical section of one embodiment of a venting mechanism for the gravitational flow system of FIG. 1.

FIG. 2 of the drawings is a vertical section of a variable venturi mechanism used in the flow rate gauge of FIG. 1.

FIG. 3 of the drawings is a schematic view of the gravitational flow system of FIG. 1, including an electronic system for indicating the flow rate of liquid within the system and a feedback for controlling the rate of such flow.

DETAILED DESCRIPTION OF THE PREFERRED EMBODIMENT

While this invention is susceptible of embodiment of many different forms, there is shown in the drawings and will herein be described in detail, several specific embodiments, with the understanding that the present disclosure is to be considered as an exemplification of the principals of the invention and is not intended to limit the invention to the embodiments illustrated.

Gravitational flow system 10 for the sequential administration of medical liquids 12, as seen in FIG. 1, includes means 14 for measuring the rate of flow of liquid 12 through system 10. System 10 includes a primary container 16 suspended in space for containing medical liquid 12. A primary tube 18 is connected to and in fluid communication with container 16. As shown, this fluid communication has taken the form of a combined piercing pin and drip chamber 20. Piercing pin 20 includes a vented port 22. However, other commonly known means of administering medical liquids, such as a collapsible container and/or an unvented system, may be used. Primary tube 18 is disposed substantially downwardly from primary container 16. On primary tube 18 is primary flow control 24, for adjustably controlling the flow of liquid 12 through system 10. In the embodiment shown, primary flow control 24 comprises a roller clamp. Again, other commonly known means of controlling liquid flow within a liquid medical system may be employed. An intravenous needle assembly 19 is connected and in fluid communication with primary tube 18 at the proximal end of primary tube 18.

As further seen in FIG. 1, gravitational flow system 10 includes mechanism 14 for measuring the rate of flow of liquid 12 within the system 10. Mechanism 14 in this embodiment comprises a secondary tube 26 having its proximal end 28 connected and in fluid communication with primary tube 18. Secondary tube 26 is disposed substantially vertically from its proximal end 28. Tertiary tube 30 has its proximal end 32 connected and in fluid communication with primary tube 18 at a point below proximal end 28 of secondary tube 26. Again, tertiary tube 30 is disposed substantially vertically from its proximal end 32. A constricting mechanism 34 is positioned about primary tube 18, at the connection between the proximal end 32 of tertiary tube 30 and primary tube 18. Constricting mechanism 34 restricts the flow of liquid 12 through primary tube 18. As a result a pressure differential is created between proximal end 28 of secondary tube 26 and proximal end 32 of tertiary tube 30. Corresponding pressure differentials are thus created within secondary tube 26 and tertiary tube 30. Consequently, the ability of each tube to sustain a column of water varies, in direct proportion to the flow of liquid 12 within primary tube 18. Between secondary tube 26 and tertiary tube 30 at their distal end is a connector mechanism 36 which is constructed and arranged for fluid communication between the two tubes. Primarily, connecting mechanism 36 is adapted for the passage of air therethrough. The passage of such air allows one column of water to rise as the other falls.

Bernoulli's principle states that pressure in a tube is inversely proportional to flow rate. As the flow of liquid in primary tube 18 increases, the column of liquid 12 within tertiary tube 30 will fall and correspondingly, the column of liquid 12 within secondary tube 26 will rise. The extent of such movement can be measured and used to indicate the rate of flow of liquid within the system 10.

In order to view the relative position of liquid within secondary tube 26 and tertiary tube 30, a portion of at least one of the tubes is substantially transparent. In a preferred embodiment, primary tube 18, secondary tube 26 and tertiary tube 30 are constructed of a flexible transparent plastic material. Disposed on secondary tube 26 and/or tertiary tube 30 are a series of markings 38, which serve as visual indicia of the relative position of liquid 12 within the tubes. From previous measurements, each marking represents a known rate of flow of liquid whereby the rate of flow of liquid within the system may be determined.

As best seen in FIG. 1A, an additional feature of the invention is venting mechanism 40 which comprises, in this embodiment, a flexible, penetrable, bulb member 42 connected to and in fluid communication with connector mechanism 36. A hollow needle or cannula 44 is fixedly attached to connector mechanism 36 and extends upwardly within flexible, penetrable bulb member 42. As a result, bulb member 42 may be selectively penetrated by cannula 44 so as to release air from within secondary tube 26 and tertiary tube 30 as desired. As a result, when liquid is being disposed into secondary tube 26 and tertiary tube 30 during priming, air may be vented through venting mechanism 30 so that liquid 12 will rise to a mid-point in both secondary tube 26 and tertiary tube 30.

An alternative embodiment of venting mechanism 40 (not shown in the drawings) is the use of a plurality of apertures disposed about port 46, covered by a cap. When the cap is removed, the apertures allow the release of air. The cap may be threadedly attached or spring-loaded on port 46 and raised when venting of air from port 46 is desired.

As further seen in FIG. 1A, an additional feature of the invention is the inclusion of a valve mechanism 48 proximate the distal end of secondary tube 26, for preventing the flow of liquid 12 from within secondary tube 26 into tertiary tube 30 by means of connector mechanism 36. Such movement of liquid 12 could conceivably result in the passage of air from tertiary tube 30 through primary tube 18, with concomitant danger to the patient. One such valve mechanism is the use of ball check valves 50 and 52 positioned within secondary tube 26 and/or tertiary tube 30 for preventing the flow of liquid 12 beyond the distal end of secondary tube 26 of tertiary tube 30. As shown, balls 50 and 52 are of greater diameter than orifices 54 and 56. Balls 50 and 52 have positive buoyancy so as to float within liquid 12. Consequently, when liquid 12 rises to the distal end of secondary tube 26 or tertiary tube 30, balls 50 and 52 correspondingly rise to the point where they block orifices 54 and 56, preventing the flow of liquid 12 therethrough.

In one embodiment of the invention, another valve mechanism 58, at the proximal end of tertiary tube 30, prevents the passage of air from tertiary tube 30 into primary tube 18. Valve mechanism 58, preferably, comprises a hydrophilic membrane sealed in and disposed at the proximal end of tertiary tube 30.

In one embodiment of the invention, secondary tube 26 and tertiary tube 30 may be connected to a pressure gauge which is used to indicate the relative difference in pressure between each tube. The corresponding rate of flow of medical liquid within the tubes may thus be determined. One embodiment of such a pressure gauge may be seen in FIG. 3. At the distal end of secondary tube 26 and tertiary tube 30 are respectively disposed a pair of pressure transducers 60 and 62 which convert the pressure within secondary tube 26 and tertiary tube 30 into an electrical signal and transmit it to electrical meter 64. Electrical meter 64 converts the electrical signals into an alpha numeric display, which may indicate either the relative pressure within each tube or a rate of flow of liquid 12 within primary tube 18. Additionally, electrical meter 64 may include a feedback system for controlling an electrically actuated valve 66 attached to primary tube 18.

Returning to FIG. 2 of the drawings, in a preferred embodiment, constrictor mechanism 34 comprises a variable venturi mechanism 68 for adjustably controlling the size of orifice 70 through primary tube 18. Adjustment of the size of orifice 70 results in a change in the sensitivity of flow rate measuring device 14. Consequently, the full length of tertiary tube 30 may be used when measuring low flow rates, in order to provide the desired visual indicia.

Variable venturi 68 comprises a screw clamp body 72 with threaded shaft 74 and nut 76 threadedly attached thereto. A rotation of nut 76 causes corresponding inward or outward movement of threaded shaft 74. As a result, tip 78 of shaft 74 either reduces or increases the size of cavity 80 within screw clamp body 72. The passage of liquid 12 through primary tube 18 is thus impeded by tip 78 when it is extended into cavity 80. Opening 82 from cavity 80 into distal end 32 of tertiary tube 30 conveys the relative change in flow rate in the form of pressure exerted against the liquid within tertiary tube 30. As cavity 80 is reduced in size, liquid 12 increases its rate of flow but decreases the amount of pressure exerted through opening 82. Consequently, the ability of tertiary tube 30 to sustain a column of liquid is reduced.

Operation of the System

Returning to FIG. 1 of the drawings, in operation, air is expelled from gravitational system 10 in the normal manner by allowing liquid 12 to flow through primary tube 18. Secondary tube 26 and tertiary tube 30 are then filled half way up with liquid 12, by allowing the air in gauge 14 to be expelled by means of piercing bulb 42 with cannula 44. Liquid 12, seeking its own level, fills secondary tube 26 and tertiary tube 30 to the mid-point. At this time bulb 42 is raised above cannula 44. Variable venturi 68 may then be set for the desired degree of sensitivity by means of markings on the exterior of screw clamp body 72 (i.e., high or low flow rate settings).

As stated previously, Bernoulli's principle states that pressure in a tube is inversely proportional to flow rate. As the flow of liquid in primary tube 18 increases, the column of liquid 12 within tertiary tube 30 will fall and correspondingly, the column of liquid 12 within secondary tube 26 will rise. The extent of such movement can be measured and used to indicate the rate of flow of liquid within the system 10.

In order to view the relative position of liquid within secondary tube 26 and tertiary tube 30, a portion of at least one of the tubes is substantially transparent. In a preferred embodiment, both primary tube 18, secondary tube 26 and tertiary tube 30 are constructed of a flexible transparent plastic material. Disposed on secondary tube 26 and/or tertiary tube 30 are a series of markings 38, which serve as visual indicia of the relative position of liquid 12 within the tubes. From previous measurements, each marking represents a known rate of flow of liquid whereby the rate of flow of liquid within the system may be determined.

Consequently, flow control 24 may be adjusted until liquid 12 within secondary tube 26 and tertiary tube 30 is maintained at the desired flow rate setting.

The foregoing description and drawings merely explain and illustrate the invention and the invention is not so limited thereto except insofar as the appended claims are so limited as those skilled in the art who have the disclosure before them will be able to make modifications and variations therein without departing from the scope of the invention.

I claim:

1. An apparatus for the measurement of the rate of flow of medical liquids within a gravitational flow system for the sequential administration of said liquids to a patient comprising:
    a primary tube having its distal end in fluid communication with the source of said medical liquid, said primary tube being disposed substantially downwardly therefrom;
    a secondary tube having its proximal end in fluid communication with said primary tube;
    constrictor means reducing the inside diameter of said primary tube at a selected point and thereby impeding the flow of liquid therethrough;
    pressure gauge means for measuring the relative difference in pressure between said secondary tube and said primary tube whereby the rate of flow of said medical liquid may be determined, said pressure gauge means comprising a pressure transducer attached to said secondary tube; and
    electrically activated valve means for controlling the rate of flow of liquid through said primary tube.

2. The invention according to claim 1 in which said constrictor means comprises a variable venturi mechanism for adjustably controlling the orifice size of said constrictor means, thereby fllowing adjustment of the sensitivity of said apparatus.

3. The invention according to claim 1 in which said variable venturi mechanism comprises a screw clamp member for adjustably compressing said primary tube and thereby constricting the flow of liquid therethrough.

4. The invention according to claim 1 further comprising venting means for dispensing air from said secondary tube whereby a desired volume of liquid may be introduced from said primary tube into said secondary tube.

5. The invention according to claim 4 in which said venting means comprises:
   a port member extending from said secondary tube means, said port member having a plurality of venting apertures thereupon;
   a cap member movably attached to said port member and covering said venting apertures, said cap member being constructed and arranged for selective exposure of said venting apertures to the atmosphere, whereby air within said secondary and tertiary tubes may be vented as desired.

6. The invention according to claim 5 in which said cap member is threadedly attached to said port member.

7. The invention according to claim 1 in which a plurality of said tubes are constructed of a flexible transparent plastic material so as to facilitate the priming and operation of said apparatus.

* * * * *

UNITED STATES PATENT AND TRADEMARK OFFICE
CERTIFICATE OF CORRECTION

PATENT NO. : 4,363,321
DATED : December 14, 1982
INVENTOR(S) : Richard M. Chittenden It is certified that error appears in the above—identified patent and that said Letters Patent is hereby corrected as shown below:

Column 6, line 59, Claim 2, should read:

constrictor means, thereby allowing adjustment of the

Signed and Sealed this

Twenty-second Day of February 1983

[SEAL]

Attest:

GERALD J. MOSSINGHOFF

Attesting Officer

Commissioner of Patents and Trademarks